United States Patent

Iwasaki et al.

Patent Number: 5,770,762
Date of Patent: Jun. 23, 1998

[54] PROCESS FOR PRODUCING 4-SUBSTITUTED-2-BUTENALS

[75] Inventors: Hideharu Iwasaki; Takashi Onishi, both of Hasaki-machi, Japan

[73] Assignee: Kuraray Co., Ltd., Kurashiki, Japan

[21] Appl. No.: 837,850

[22] Filed: Apr. 22, 1997

[30] Foreign Application Priority Data

Apr. 24, 1996 [JP] Japan .................................. 8-127789

[51] Int. Cl.⁶ ........................... C07C 45/45; C07C 67/00
[52] U.S. Cl. ........................ 560/238; 568/433; 568/459; 568/463; 560/231
[58] Field of Search .................................. 560/238, 231; 568/433, 459, 463

[56] References Cited

U.S. PATENT DOCUMENTS 4,873,362  10/1989  Merger et al. ......................... 560/238

FOREIGN PATENT DOCUMENTS 36 39 562  6/1988  Germany .

OTHER PUBLICATIONS

Carlos F. Barbas, et al., Journal of the American Chemical Society, vol. 112, No. 5, pp. 2013–2014, "Deoxyribose–5–Phosphate Aldolase as a Synthetic Catalyst", Feb. 28, 1990.
Barbas et al., "Deoxyribose–5–phosphate . . . catalyst", J. Am. Chem. Soc., 112(5), pp. 2013–2014, 1990.

*Primary Examiner*—Gary Geist
*Assistant Examiner*—Rosalynd Kerp
*Attorney, Agent, or Firm*—Oblon, Spivak, McClelland, Maier & Neustadt, P.C.

[57] ABSTRACT

Described is a process for producing a 4-substituted-2-butenal represented by the following formula (1);

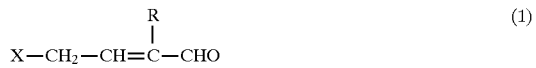

(wherein X represents an acyloxy group or halogen atom; R represents hydrogen atom, an aliphatic hydrocarbon group or an aromatic hydrocarbon group; and these hydrocarbon groups can be substituted with hydroxyl group, an alkoxy group, an aryloxy group, an acyl group or an alkoxycarbonyl group), which is useful as synthetic intermediates of phormaceutieals, agricultural chemicals and the like, comprising subjecting a substituted acetaldehyde represented by the following formula (2);

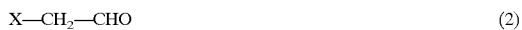

(wherein X has the same meaning as defined above), with an aldehyde represented by the following formula (3);

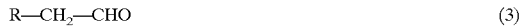

(wherein R has the same meaning as defined above) in the presence of an amino carboxylic acid.

21 Claims, No Drawings

PROCESS FOR PRODUCING 4-SUBSTITUTED-2-BUTENALS

BACKGROUND OF THE INVENTION

1. Field of the Invention

The present invention relates to a process for producing 2-butenals with an acyloxy group or a halogen atom at 4-position as the substituent (abbreviated as "4-substituted-2-butenals" hereinbelow).

The 4-substitued-2-butenals produced by the process of the present invention are useful as synthetic intermediates of pharmaceuticals, agricultural chemicals and the like. For example, 4-acetoxy-2-methyl-2-butenal is a key compound for producing vitamin A acetate (see Pure & Appl. Chem., 63, 45(1991); British Patent No. 1168639 and the like). In addition, 4-chloro-2-methyl-2-butenal can be converted readily into the above described 4-acetoxy-2-methyl-2-butenal by the treatment with potassium acetate [see J. Org. Chem., 42, 1648(1976) and the like].

2. Related Art of the Invention

A variety of processes have been known as the process for producing 4-substituted-2-butenals. As to the process for producing 4-acetoxy-2-methyl-2-butenal, for example, the following processes have been known.

i) A process comprising converting 1,4-dihydroxy-2-butene into 3,4-dihydroxy-1-butene by rearrangement, acetylating the 3,4-dihydroxy-1-butene to give 3,4-diacetoxy-1-butene, hydroformylating the 3,4-diacetoxy-1-butene and eliminating one acetoxy group from the hydroformylation product (see U.S. Pat. No. 3,840,589).

ii) A process comprising ethynylating methylglyoxal dimethyl acetal, partially hydrogenating the resulting product to give 2-hydroxy-2-methyl-3-butenal dimethyl acetal, acetylating the 2-hydroxy-2-methyl-3-butenal dimethyl acetal to give 2-acetoxy-2-methyl-3-butenal dimethyl acetal and converting the 2-acetoxy-2-methyl-3-butenal dimethyl acetal into 4-acetoxy-2-methyl-2-butenal dimethyl acetal by rearrangement in the presence of copper catalyst, followed by selective hydrolysis (see U.S. Pat. No. 3,639,437).

iii) A process comprising subjecting propanal to the reaction with acetoxyacetaldehyde in the presence of a secondary amine and an organic acid (see U.S. Pat. No. 4,873,362).

In addition, as to the process for producing 4-chloro-2-methyl-2-butenal, the following processes have been known.

iv) A process comprising oxidizing isoprene with an organic peracid such as peracetic acid in ethyl acetate to give 2-methyl-2-vinyloxirane and chlorinating the 2-methyl-2-vinyloxirane in the presence of copper chloride and lithium chloride [see J. Org. Chem., 41, 1648(1976)].

v) A process comprising chlorinating the above-described 2-methyl-2-vinyloxirane with acetyl chloride and alumina under gas-phase conditions (see U.S. Pat. No. 4,054,608).

vi) A process comprising oxidizing prenyl chloride with selenium dioxide [see Nippon Kagaku Kaishi, Vol.12, pp.2246 (1975)].

However, the processes i) and ii) require a number of reaction steps. Also, the process iii) requires the use of secondary amine and organic acid as the catalysts at 20 to 100 mol % based on the starting acetoxyacetaldehyde, in order to obtain the objective compound at a higher yield. However, the yield of the objective compound according to the process iii) is 42% to 63%.

The processes iv) and v) require the use of an organic peracid, which is explosive, during the preparation of 2-methyl-2-vinyloxirane; and the processes have the problem of the corrosion of reaction apparatus during the halogenation. Also, the process vi) requires the use of highly toxic selenium dioxide at an equimolar amount to the amount of the starting material.

As has been described above, the conventionally known processes for producing 4-substituted-2-butenals are disadvantageous for industrial practice.

SUMMARY OF THE INVENTION

An object of the present invention is to provide a process for producing 4-subtituted-2-butenals industrially advantageously in a simple manner.

The object of the present invention can be achieved by a process described hereinbelow.

More specifically, the present invention is a process for producing a 4-substituted-2-butenal represented by the following formula (1);

(wherein X represents an acyloxy group or halogen atom; R represents hydrogen atom, an aliphatic hydrocarbon group or an aromatic hydrocarbon group; and these hydrocarbon groups can be substituted with hydroxyl group, an alkoxy group, an aryloxy group, an acyl group or an alkoxycarbonyl group), comprising subjecting a substituted acetaldehyde represented by the following formula (2);

(wherein X has the same meaning as defined above), to the reaction with an aldehyde represented by the following formula (3);

(wherein R has the same meaning as defined above) in the presence of an amino carboxylic acid.

DETAILED DESCRIPTION OF THE INVENTION

The present invention is described in more detail.

In the above formula (2) which represents a substituted acetaldehyde used as one starting material, the acyloxy group represented by X includes, for example, aliphatic acyloxy groups such as acetoxy group, propionyloxy group, butyryloxy group, isobutyryloxy group, valeryloxy group, isovaleryloxy group, pivaloyloxy group, octoyloxy group, lauroyloxy group myristoyloxy group, palmitoyloxy group and stearoyloxy group; and aromatic acyloxy groups such as benzoyloxy group, p-toluoyloxy group and p-chlorobenzoyloxy group. Among them, those with 1 to 20 carbon atoms are preferred.

In the formula (2), examples of the halogen atom represented by X include chlorine atom or bromine atom.

Specific examples of the substituted acetaldehyde represented by the formula (2) include acetoxyacetaldehyde, propionyloxyacetaldehyde, isovaleryloxyacetaldehyde, octoyloxyacetaldehyde and chloroacetaldehyde. Among these compounds, acetoxyacetaldehyde and chloroacetaldehyde are preferable.

As the substituted acetaldehyde represented by the formula (2), commercially available ones can be used; or those produced by the known processes can also be used. For example, acetoxyacetaldehyde, which is the substituted acetaldehyde of the formula (2) wherein X is acetoxy group, can be produced readily by a process comprising ozonolysis of 1,4-diacetoxy-2-butene (see U.S. Pat. No. 5,543,560) and the like.

In the formula (3), which represents an aldehyde used as another starting material, the aliphatic hydrocarbon groups represented by R include, for example, alkyl groups such as methyl group, ethyl group, propyl group, isopropyl group, isoamyl group and n-octyl group; alkenyl groups such as allyl group; alkynyl groups such as propargyl group; and cycloalkyl groups such as cyclohexyl group and cyclooctyl group. Among them, those with 1 to 20 carbon atoms are preferable; those with 1 to 12 carbon atoms are more preferable; and methyl group is most preferable. In addition, the aromatic hydrocarbon groups represented by R include, for example, aryl groups such as phenyl group, tolyl group and naphthyl group; and aralkyl groups such as benzyl group and phenethyl group. Among them, those with 6 to 12 carbon atoms are preferable.

These aliphatic hydrocarbon groups or aromatic hydrocarbon groups can be substituted with, for example, hydroxyl group; alkoxy groups such as methoxy group, ethoxy group, isopropoxy group, isobutoxy group and isopentyloxy group; aryloxy groups such as phenoxy group; acyl groups such as acetyl group, propionyl group and benzoyl group; and alkoxycarbonyl groups such as methoxycarbonyl group and ethoxycarbonyl group.

Specific examples of the aldehyde represented by the formula (3) include acetaldehyde, propanal, butanal, pentanal, 4-pentenal, 3-methylbutanal, 3-phenylpropanal, 3-anisylpropanal, 4-hydroxybutanal, 4-acetoxybutanal and ester derivatives of 3-formylpropionic acid. Among them, propanal is preferable.

The aldehyde represented by the formula (3) can be used without specific limitation, but from the viewpoint of the yield, reaction efficiency and cost of production of the 4-substituted-2-butenals, the aldehyde is used generally in an amount of 1 to 10 moles, preferably in an amount of 1 to 2 moles, per one mole of the substituted acetaldehyde represented by the formula (2).

In the present invention, an amino carboxylic acid is used as the catalyst. The amino carboxylic acid used in the present invention means a compound having both amino group (—NH$_2$) and carboxyl group. Examples of the amino carboxylic acid include glycine, alanine, β-alanine, valine, leucine, isoleucine, serine, cysteine, methionine, threonine, tyrosine, α-aminobutyric acid, β-aminobutyric acid, phenylalanine, aspartic acid, sodium aspartate, potassium aspartate, glutamic acid, sodium glutamate and potassium glutamate. Among them, alanine, glycine, glutamic acid and aspartic acid are preferable.

If a compound having both mono- or di-N-substituted amino group and carboxylic group is used in place of the amino carboxylic acid in the present invention, side reactions such as dimerization of the substituted acetaldehyde represented by the formula (2) have occurred to reduce the yield of 4-substituted-2-butenals represented by the formula (1).

In the present invention, the amino carboxylic acid is generally used in an amount of 0.01 to 50 mol % based on the amount of the substituted acetaldehyde represented by the formula (2). From the viewpoint of the reaction efficiency and cost of production of the 4-substituted-2-butenals, the amino carboxylic acid is used in an amount of preferably 0.1 to 10 mol %, more preferably 0.5 to 5 mol %, based on the amount of the substituted acetaldehyde represented by the formula (2).

In the present invention, a carboxylic acid with no functional group other than carboxyl group (abbreviated as "carboxylic acid" hereinbelow) or the salt thereof is preferably used in combination with the amino carboxylic acid, to make the reaction proceed smoothly. Examples of such carboxylic acid include mono carboxylic acid, dicarboxylic acid and poly basic carboxylic acid, such as acetic acid, propionic acid, butanoic acid, 2-methylpropionic acid, pentanoic acid, 3-methylbutanoic acid, oxalic acid, malonic acid, succinic acid and adipic acid.

In addition, examples of the salts of the carboyxlic acid include ones with alkali metals such as sodium and potassium and ones with alkali earth metals such as calcium.

The carboxylic acid or the salt thereof can be used generally in an amount of 0.01 to 100 mol % based on the substituted acetaldehyde represented by the formula (2). From the viewpoint of the reaction efficiency and the cost of production of the 4-substituted-2-butenals, the carboxylic acid or the salt thereof is preferably used in an amount of 0.1 to 10 mol % based on the substituted acetaldehyde represented by the formula (2).

In the present invention, a solvent is not necessary, but can be used as long as it does not inhibit the reaction.

Examples of the solvent include water; saturated aliphatic hydrocarbons such as pentane, hexane, heptane and octane; aromatic hydrocarbons such as benzene, toluene and xylene; halogenated hydrocarbons such as dichloromethane, dichloroethane, chloroform and carbon tetrachloride; and ethers such as diethyl ether and diisopropyl ether.

The solvent can be used generally in an amount of 0.001 to 2 fold the weight of the substituted acetaldehyde represented by the formula (2). From the viewpoint of the reaction efficiency and the cost of production of the 4-substituted-2-butenals, the solvent is preferably used in an amount of 0.01 to 1 fold the weight of the substituted acetaldehyde represented by the formula (2).

The process of the present invention is preferably carried out in an atmosphere of an inert gas such as nitrogen and argon.

In the present invention, the reaction mechanism of the substituted acetaldehyde represented by the formula (2) with the aldehyde represented by the formula (3) is not clearly elucidated, but it is found by the inventors that an aldol condensate represented by the following formula (4);

(wherein R and X has the same meaning as defined above) is formed as an intermediate. Therefore, 4-substituted-2-butenals are considered to be formed from the above intermediate.

The process of the present invention is generally carried out as follows.

The process is carried out by charging a reaction vessel equipped with an agitator with the substituted acetaldehyde represented by the formula (2), the aldehyde represented by the formula (3), an amino carboxylic acid, a carboxylic acid or the salt thereof if desired, and a solvent if necessary, followed by agitation at a given temperature. The process is also carried out by charging a reaction vessel equipped with an agitator with the aldehyde represented by the formula (3), an amino carboxylic acid, a carboxylic acid or the salt thereof if desired, and a solvent if necessary, and adding the substituted acetaldehyde represented by the formula (2) into the resulting mixture, followed by agitation at a given temperature.

The progress of the reaction can be checked by detecting the starting materials and the intermediate with conventional means such as gas chromatography.

In addition, the process of the present invention can be carried out stepwise by removing the excessive substituted acetaldehyde represented by the formula (2) or the aldehyde represented by the formula (3) under atmospheric pressure or reduced pressure to obtain the residue containing the intermediate, and then agitating the resulting residue at a given temperature.

The reaction temperature is generally within a range of 10° to 200° C., preferably within a range of 50° to 150° C., while the reaction time is generally 4 to 12 hours. The reaction can be carried out under atmospheric pressure, reduced pressure or elevated pressure.

After completion of the reaction, 4-substituted-2-butenals can be is isolated by a known method, for example, comprising pouring the reaction mixture into water, extracting the product with an organic solvent such as dichloromethane and ethyl acetate, and removing the organic solvent from the extract under atmospheric pressure or reduced pressure.

The 4-substituted-2-butenals thus obtained can be further purified by known means such as distillation under reduced pressure or chromatography.

Furthermore, the process of the present invention can be carried out stepwise comprising isolating the intermediate and converting the intermediate into 4-substituted-2-butenals.

In this case, the process of the present invention is carried out as described below.

In the same manner as described above, the substituted acetaldehyde represented by the formula (2) is subjected to the reaction with the aldehyde represented by the formula (3) in the presence of an amino carboxylic acid, and the intermediate is isolated from the reaction mixture by known methods such as distillation or extraction with an organic solvent, after the starting materials have disappeared. For the extraction, organic solvents such as dichloromethane and ethyl acetate can be used.

Then, the intermediate is heated at 50° to 160° C. to give readily 4-substituted-2-butenals. The time for the above heating process is generally within a range of 2 to 4 hours. In the above heating process, the aforementioned carboxylic acid or the salt thereof can preferably be added to the intermediate.

After completion of the reaction, the reaction mixture is treated in the same manner as described above to isolate the 4-substituted-2-butenals.

According to the present invention, 4-substituted-2-butenals can be produced easily in good yield. The process of the present invention is useful as a process for producing 4-substituted-2-butenals on an industrial scale.

Other features of the present invention will become apparent in the course of the following descriptions of exemplary embodiments which are given for illustration of the present invention and are not intended to be limiting thereof.

EXAMPLES

Example 1

A 300-ml three-necked flask was charged with 43 g of propanal (0.74 mole), 0.2 g of alanine (2 mmol), 0.4 g of acetic acid and 1.6 g of water, and then, the inner temperature was heated to 60° C. under agitation. To the resulting mixture, 40 g of acetoxyacetaldehyde (0.39 mol) was added dropwise over 2 hours. After completion of the addition, the reaction mixture was agitated at the same temperature for 4 hours, while checking the progress of the reaction by the analysis of a small portion of the reaction mixture with gas chromatography under the following conditions, to confirm the disappearance of the acetoxyacetaldehyde.

Excessive propanal was distilled off from the resulting reaction mixture under atmospheric pressure. Then, the resulting residue was agitated at 80° C. for 4 hours, while checking the progress of the reaction by the analysis of a small portion of the reaction mixture with gas chromatography under the following conditions, to confirm the disappearance of the intermediate (retention time; 16 minutes). At the completion of the reaction, 40.7 g of 4-acetoxy-2-methyl-2-butenal was formed.

After cooling the resulting mixture to room temperature, 10 g of aqueous 5% sodium bicarbonate was added to the mixture and, after thorough shaking, the organic layer was separated. The resulting organic layer was distilled under reduced pressure to give a crude product, which was further purified by distillation under reduced pressure to give 39.2 g of 4-acetoxy-2-methyl-2-butenal (boiling point of 83°–85° C./1 mmHg; yield: 70.5%).

The conditions for gas chromatographic analysis are as follows.

Column: OV-17, 3 m×4 mmφ (made by GL Science INC.)
Temperature of column: raised to 240° C. from 70° C. (rate of temperature rise: 5° C./minute)
Detector: FID detector

Example 2

The general procedure of Example 1 was repeated except that 0.2 g (3 mmol) of glycine was used instead of 0.2 g of alanine to give 36.9 g of 4-acetoxy-2-methyl-2-butenal (yield: 66.3%).

Example 3

The general procedure of Example 1 was repeated except that 0.3 g (2.5 mmol) of glutamic acid was used instead of 0.2 g of alanine to give 33.2 g of 4-acetoxy-2-methyl-2-butenal (yield: 59.4%).

Comparative Example 1

The general procedure of Example 1 was repeated except that 0.2 g (1.4 mmol) of N-methylalanine was used instead of 0.2 g of alanine. Three hours after completion of the dropwise addition of acetoxyacetaldehyde, the reaction mixture was analyzed by gas chromatography under the same conditions as in Example 1. However, no 4-acetoxy-2-methyl-2-butenal was found.

Examples 4 to 6

The general procedure of Example 1 was repeated using a substituted acetaldehyde represented by the formula (2) and an aldehyde represented by the formula (3), having X and R shown in Table 1, in an amount of the same moles as in Example 1 to give corresponding 4-substituted-2-butenal. The yields of the objective compounds (determined by the internal standard method with gas chromatography under the same conditions as in Example 1) are shown in Table 1.

The objective compounds were isolated by column chromatography on silica gel (eluent: hexane/ethyl acetate=9/1 (v/v ratio)).

TABLE 1

|  | X | R | Yield (%) |
|---|---|---|---|
| Example 4 | Propionyloxy group | Methyl group | 69.3 |
| Example 5 | Isobutyryloxy group | Methyl group | 68.2 |
| Example 6 | Acetoxy group | Ethyl group | 70.1 |

Example 7

A 300-ml three-necked flask was charged with 58 g of propanal (1 mole), 0.2 g of alanine, 0.4 g of sodium acetate and 1.6 g of water, and then, the inner temperature was heated to 60° C. under agitation. To the resulting mixture, 98.1 g of aqueous chloroacetaldehyde [containing 39 g (0.5 mol) of chloroacetaldehyde] was added dropwise over 2 hours. After completion of the addition, the reaction mixture was agitated at the same temperature for 6 hours, while checking the progress of the reaction by the analysis of a small portion of the reaction mixture with gas chromatography under the same conditions as in Example 1, to confirm the disappearance of the chloroacetaldehyde.

Excessive propanal was distilled off from the resulting reaction mixture under atmospheric pressure. Then, the resulting residue was agitated at 80° C. for 8 hours, while checking the progress of the reaction by the analysis of a small portion of the reaction mixture with gas chromatography under the same conditions as in Example 1, to confirm the disappearance of the intermediate (retention time; 12 minutes). At the completion of the reaction, 28.8 g of 4-chloro-2-methyl-2-butenal was formed.

After cooling the resulting mixture to room temperature, 10 g of aqueous 5% sodium bicarbonate was added to the mixture and, after thorough shaking, the organic layer was separated. The resulting organic layer was distilled under reduced pressure to give a crude product, which was further purified by distillation under reduced pressure to give 26.9 g of 4-chloro-2-methyl-2-butenal (boiling point of 40°–42° C./ 0.5 mmHg; yield: 66.3%).

Example 8

A 300-ml three-necked flask was charged with 43 g of propanal (0.74 mole), 0.2 g of alanine, 0.4 g of acetic acid and 1.6 g of water, and then, the inner temperature was heated to 60° C. under agitation. To the resulting mixture, 40 g of acetoxyacetaldehyde (0.39 mol) was added dropwise over 2 hours. After completion of the addition, the reaction mixture was agitated at the same temperature for 4 hours, while checking the progress of the reaction by the analysis of a small portion of the reaction mixture with gas chromatography under the same conditions as in Example 1, to confirm the disappearance of the acetoxyacetaldehyde.

10 g of aqueous 5% sodium bicarbonate was added into the reaction mixture and, after thorough shaking, the organic layer was separated. The resulting organic layer was distilled under reduced pressure to give 59.2 g of a fraction (boiling point of 100° to 105° C./1 mmHg). Gas chromatographic analysis of the fraction under the same conditions as in Example 1 shows a single a peak with a retention time of 16 minutes.

The infrared absorption spectrum and mass spectrum (GC-MS) of the fraction are shown below.

Infrared absorption spectrum (ν:cm$^{-1}$): 3475(O—H), 3000 (C—H), 2950(C—H), 2900, 1740(C=O), 1460, 1440, 1380, 1240(C-O), 1160(C-O), 1120, 1050, 980, 930, 620.
Mass spectrum:
160(M$^+$), 142([M—H$_2$O]$^+$), 83([M—H$_2$O—CH$_3$COO]$^+$).

The above results indicate that the fraction contains 4-acetoxy-3-hydroxy-2-methylbutanal.

0.1 g of acetic acid was added to the intermediate (59.2 g), followed by heating at 70° C. for 2 hours. The reaction mixture was analyzed by gas chromatography under the same conditions as in Example 1 to find that the intermediate had disappeared and 44.0 g of 4-acetoxy-2-methyl-2-butenal was formed (yield: 80.2%; determined by internal standard-method with gas chromatography under the same conditions as in Example 1).

Obviously, numerous modifications and variations are possible in light of the above teachings. It is therefore to be understood that within the scope of the appended claims the present invention may be practiced otherwise than as specifically described herein.

What is claimed is:

1. A process for producing a 4-substituted-2-butenal having the formula (1):

wherein X is acyloxy or halogen; R is hydrogen, aliphatic hydrocarbon group or aromatic hydrocarbon group; each of which hydrocarbon groups may be substituted with hydroxyl, alkoxy, aryloxy, acyl or alkoxycarbonyl;

which process comprises reacting a substituted acetaldehyde of the formula (2):

wherein X is as defined above, with an aldehyde having the formula (3):

wherein R is as defined above, in the presence of an amino carboxylic acid selected from the group consisting of glycine, alanine, β-alanine, valine, leucine, isoleucine, serine, cysteine, methionine, threonine, tyrosine, α-aminobutyric acid, β-aminobutyric acid, phenylalanine, aspartic acid, sodium aspartate, potassium aspartate, glutamic acid, sodium glutamate and potassium glutamate.

2. The process of claim 1, wherein the amino carboxylic acid is used in an amount of about 0.01–50 mol % based on the amount of the substituted acetaldehyde of the formula (2).

3. The process of claim 1, wherein the reaction of the substituted acetaldehyde of the formula (2) with the aldehyde of the formula (3) is effected in the presence of an amino carboxylic acid and a carboxylic acid with no functional group other than carboxyl group or a salt thereof.

4. The process of claim 3, wherein the carboxylic acid or a salt thereof is used in an amount of about 0.01–100 mol % based on the amount of the substituted acetaldehyde of the formula (2).

5. The process of claim 1, wherein the reaction of the substituted acetaldehyde of the formula (2) with the aldehyde of the formula (3) is effected stepwise by separating or isolating an intermediate containing a compound having the formula (4):

 (4)

wherein X is acyloxy or halogen; R is hydrogen, aliphatic hydrocarbon or aromatic hydrocarbon; each of which hydrocarbon groups may be substituted with hydroxy, alkoxy, aryloxy, acyl or alkoxycarbonyl; and b) converting the intermediate into a 4-substituted-2-butenal.

6. The process of claim 1, where X in formula (1) or (2) is $C_1$–$C_{20}$ acyloxy.

7. The process of claim 6, wherein X in formula (1) or (2) comprises acetoxy, propionyloxy, butyryloxy, isobmtyryloxy, valeryloxy, isovaleryloxy, pivaloyloxy, octoyloxy, lauroyloxy, myristoyloxy, palmitoyloxy, stearyloyloxy, benzoyloxy, p-toluoyloxy and p-chlorobenzoyloxy.

8. The process of claim 1, wherein X in formula (1) or (2) is halogen selected from the group consisting of chloro and bromo.

9. The process of claim 1, wherein said acetaldehyde of the formula (2) is selected from the group consisting of acetoxyaldehyde, propionyloxyaldehyde, isovaleryloxyaldehyde, octoyloxyacetaldehyde and chloroacetaldehyde.

10. The process of claim 1, wherein R is formula (3) is $C_1$–$C_{20}$ alkyl, alkenyl or cycloalkyl.

11. The process of claim 10, wherein R in formula (3) is selected from the group consisting of methyl, ethyl, propyl, isopropyl, isoamyl, n-octyl, allyl, propargyl, cyclohexyl and cyclooctyl.

12. The process of claim 1, wherein R is formula (3) is $C_6$–$C_{12}$ aromatic hydrocarbon.

13. The process of claim 12, wherein R in formula (3) is selected from the group consisting of phenyl, tolyl, naphthyl, benzyl and phenethyl.

14. The process of claim 1, wherein R in formula (3) is substituted by alkoxyl selected from the group consisting of methoxy, ethoxy, iso-propoxy, iso-butoxy and iso-pentyloxy.

15. The process of claim 1, wherein R in formula (3) is substituted by hydroxy.

16. The process of claim 1, wherein R is formula (3) is substituted by acyl selected from the group consisting of acetyl, propionyl and benzoyl.

17. The process of claim 1, wherein R is formula (3) is substituted by alkoxycarbonyl selected from the group consisting of methoxycarbonyl and ethoxycarbonyl.

18. The process of claim 1, wherein the aldehyde of the formula (3) is selected from the group consisting of acetaldehyde, propanol, butanal, pentanal, 4-pentanal, 3-methylbutanal, 3-phenylpropanal, 3-anisylpropanal, 4-hydroxybutanal, 4-acetoxybutanal and an ester of 3-formylpropionic acid.

19. The process of claim 3, wherein said carboxylic acid having no functional group other than carboxyl is selected from the group consisting of acetic acid, propionic acid, butanoic acid, 2-methylpropionic acid, pentanoic acid, 3-methylbutanoic acid, oxalic acid, malonic acid, succinic acid and adipic acid and alkali metal and alkaline earth salts thereof.

20. The process of claim 1, wherein said reaction is carried out at from about 10° to 200° C.

21. The process of claim 20, wherein said reaction is carried out at from about 50° to 150° C.

* * * * *